(12) United States Patent
Mu (10) Patent No.: US 7,563,245 B2
(45) Date of Patent: Jul. 21, 2009

(54) SYRINGE FOR POWDER MEDICAMENT PREMIXING

(76) Inventor: Limin Mu, Room 107, No. 8, Kangle Avenue, Torch Development Zone, Zhongshan City (CN) 528437

( * ) Notice: Subject to any disclaimer, the term of this patent is extended or adjusted under 35 U.S.C. 154(b) by 231 days.

(21) Appl. No.: 10/595,825

(22) PCT Filed: Aug. 10, 2004

(86) PCT No.: PCT/CN2004/000924

§ 371 (c)(1),
(2), (4) Date: Aug. 9, 2006

(87) PCT Pub. No.: WO2005/049166

PCT Pub. Date: Jun. 2, 2005

(65) Prior Publication Data

US 2007/0129671 A1    Jun. 7, 2007

(30) Foreign Application Priority Data

Nov. 21, 2003  (CN) .................... 2003 2 0109812 U
Nov. 21, 2003  (CN) .................... 2003 2 0109813 U
May 9, 2004    (CN) .................... 2004 2 0041883 U
Jun. 23, 2004  (CN) .................... 2004 2 0042084 U (51) Int. Cl.
*A61M 37/00*   (2006.01)
*A61M 5/20*    (2006.01)
*A61M 5/28*    (2006.01)
*A61M 5/315*   (2006.01)

(52) U.S. Cl. .............................. 604/82; 604/89; 604/209
(58) Field of Classification Search .................... 604/68, 604/82–92, 195
See application file for complete search history.

(56) References Cited

U.S. PATENT DOCUMENTS

| 5,520,639 | A | * | 5/1996 | Peterson et al. ............... 604/68 |
| 5,637,087 | A | | 6/1997 | O'Neil et al. |
| 6,319,225 | B1 | | 11/2001 | Sugita et al. |
| 6,776,775 | B1 | * | 8/2004 | Mohammad ................ 604/195 |
| 6,902,543 | B1 | * | 6/2005 | Cherif-Cheikh et al. ....... 604/82 |

FOREIGN PATENT DOCUMENTS

| CN | 1066397 | 11/1992 |
| CN | 1125623 | 7/1996 |
| CN | 2612384 Y | 4/2004 |
| JP | 2001104482 | 4/2001 |

* cited by examiner

*Primary Examiner*—Nicholas D Lucchesi
*Assistant Examiner*—Imani Hayman
(74) *Attorney, Agent, or Firm*—Knoble Yoshida & Dunleavy, LLC (57) ABSTRACT

The present invention is directed to an assembled syringe for administering powder medicament in the field of medicine. By using a connecting tube, a solvent bottle containing diluent communicates with a solute bottle containing powder by external force, and the diluent is injected into the solute bottle through the connecting tube under pressure. After the powder is dissolved and mixed uniformly, the mixed solution is injected directly into a patient or added to a transfusion bottle or tube. Both the solvent and solute bottles are packaged into a sleeve to avoid contamination. Buckles on the plunger sleeve are fitted into restricting slots on the sleeve. The fitting of the slots and buckles restricts the position of the syringe, self-locking and controlling the magnitude of force by which the solute bottle is communicated with the solvent bottle, controlling the depth of insertion of the needle into the body, and preventing misoperation or damage during transport, fetching and using.

10 Claims, 6 Drawing Sheets

SYRINGE FOR POWDER MEDICAMENT PREMIXING

RELATED APPLICATIONS

This application is a national stage application, pursuant to 35 U.S.C. section 371, of International Application No. PCT/CN2004/000924 filed 10 Aug. 2004, which claims priority to CN 200320109812.7 filed 21 Nov. 2003; CN 200320109813.1 filed 21 Nov. 2003; CN 200420041883.2 filed 9 May 2004; and CN 200420042084.7 filed 23 Jun. 2004.

BACKGROUND OF THE INVENTION

1. Field of the Invention

The present invention is directed to syringes in the field of medicine, especially to an assembled syringe for administering powder medicament. According to the present invention a solvent bottle containing diluent communicates with a solute bottle containing powder via a connecting tube. The diluent is injected into the solute bottle through the connecting tube using pressure. After the powder is dissolved and mixed uniformly with the diluent, the mixed solution is injected directly into a patient or added to a transfusion bottle or a transfusion tube. Both the solvent bottle and the solute bottle are packaged into a sleeve to avoid contamination or cross-infection. Buckles provided on the plunger sleeve are fitted into restricting slots. The fitting of the slots and buckles restricts the syringe position, self-locking and controlling the magnitude of force by which the solute bottle communicates with the solvent bottle. This also allows control of the depth of insertion of the needle into the body, and prevents misoperation or damage during transport, fetching and using. The present invention is a novel design with industrial applicability and can be adapted to generalized use in the industries.

2. Description of the Related Technology

Conventionally in medical applications, syringes, vials and diluents are separately provided. When a nurse is preparing to inject powder medicament, such as penicillin, into the body of a patient, he/she has to pierce the needle of a syringe into a vial containing diluent, draw out the diluent into the syringe, pierce the needle of the syringe into a different vial containing the powder medicament, inject the diluent from the first vial into the second vial to dissolve the powder, then draw the mixed solution into the syringe again before administering it to the patient or adding it to a transfusion bottle or transfusion tube for bolus intravenous injection. The operation involves several medical components and is complicated. Contamination of the syringe or mishandling of the medicament may result. Such syringes must be handled with great care and skill, which may put a nurse operating the syringe under great stress.

A Chinese patent application entitled "Vial Type Pressurized Syringe for Powder Medicament" filed by some of the present inventors discloses a syringe structure that punctures an inner bladder of a vial containing the powder medicament by a needle provided on the front end of a plunger to uniformly mix the powder medicament under pressure with a diluent contained in a solute bottle before injection. This syringe structure is advantageous by its simplified structure but the following defects have been found during its use:

1. The inner bladder and the solute bottle are not provided with protective jackets and the inner ends of the inner bladder and the solute bottle are not provided with seal stoppers. The needle is not provided with a sheath. Contamination or cross-infection tends to happen due to poor sealing.

2. When a nurse is operating the syringe, it is very difficult for him/her to control the force applied to the plunger and the depth of injection of the needle.

3. The distance between the inner bladder and the solute bottle is very short, thus causing problems such as sway or damage due to engagement with each other. There may also be unintended communication during transportation, handling or operation.

SUMMARY OF THE INVENTION

It is an object of the present invention to provide a syringe for premixing and administering powder medicament with novel design to overcome the drawbacks of existing syringes that are prone to contamination and cross-infection. The syringe according to the present invention is more practical and cost effective with considerable industrial applicability.

It is another object of the present invention to provide a syringe for premixing and administering powder medicament with novel design to overcome the problem of existing syringes that are difficult to operate and control. The syringe according to the present invention is easy to operate with shortened traveling distance of the needle, making the force applied to the plunger and injection depth of the needle easy to control.

It is yet another object of the present invention to provide a syringe for premixing and administering powder medicament with novel design to overcome the problem of loose fitting between the inner bladder and the solute bottle which can cause damage during transportation and handling by providing a locking configuration.

It is still yet another object of the present invention to provide a syringe for premixing and administering powder medicament with novel design to overcome the problem of return flow of the mixed medicament and the returning to the original position of the bracket after moving due to the pressure generated after the bracket has been pulled out.

The above and other objects of the present invention and the resolution of the technical problems are achieved by the following technical solutions. A syringe for power medicament premixing according the present invention comprises a plunger, a sleeve, a solvent bottle, a connecting tube, a solute bottle and a syringe needle with two piercing ends, in which the plunger is provided on the upper portion of the sleeve and the solvent bottle. Both the solvent bottle and the solute bottle are packaged in the sleeve, wherein the solvent bottle is provided above the solute bottle. A syringe needle having two piercing ends is connected to the bottom portion of the solute bottle. A hollow connecting tube with two piercing ends is provided between the solvent bottle and the solute bottle. One piercing end of the connecting tube is fixed to a bracket plugged into a bottom opening of the solvent bottle. At least two protrusions are formed on the inner side of the bracket. The protrusions are in contact with the bottom opening of the solvent bottle. The central portion of the solvent bottle and the sealing plug are provided with a guiding recess. The bottom opening of the solute bottle is also provided with a sealing plug made of surgical rubber or innoxious rubber. A guiding recess is provided at the central portion of the sealing plug. A piston is provided inside the solute bottle. One piercing end of the syringe needle with two piercing ends is fixed to a bracket plugged into the bottom opening of the solute bottle. At least two protrusions are formed on the inner side of the bracket. The protrusions are in contact with the bottom opening of the solute bottle. The sealing plug, bracket and the syringe needle with two piercing ends are covered with a protecting jacket. The protrusions can be in any form of a nipple, a fin or a hook.

The above and other objects of the present invention may be further achieved by the following technical solutions.

Said syringe for powder medicament premixing according to the present invention, in which the solvent bottle is applied with inner pressure and provided inside an inner sleeve. The inner sleeve is inserted into the solute bottle, and both the solute bottle and the inner sleeve are arranged inside the sleeve. The lower end face of the inner sleeve formed with holes is in contact with a piston.

Said syringe for powder medicament premixing according to the present invention, in which the inside of said solvent bottle is of normal pressure. A piston is provided on the upper end of the solvent bottle and under the plunger, wherein the solvent bottle is inserted into the solute bottle, or the solute bottle is inserted into the solvent bottle, or the outer diameters of the solvent bottle and the solute bottle are identical and a pushing sleeve is provided on the upper edge of the piston inside the solute bottle.

Said syringe for powder medicament premixing according to the present invention, in which the solvent bottle is pressurized internally. Said sleeve is provided with restricting slots. The restricting slots comprise a first restricting slot and a second restricting slot, which are upside-down "L"-shaped and communicate with each other. A plunger sleeve integrated with the plunger is provided with buckles vertical to the plunger sleeve. The buckles are fitted into the first restricting slot or the second restricting slot. Two tongues are arranged on the two sides of the lower edge of the plunger sleeve and symmetrical to the axis thereof. Two slots corresponding to the positions of the tongues are arranged on the two sides of the upper edge of the inner sleeve and symmetrical to the axis thereof. The cross-section of the sleeve is of round shape, square shape, rectangular shape, ellipse shape, triangle shape, pentagon shape, or hexagon shape but with inner round shape, etc.

Said syringe for powder medicament premixing according to the present invention, in which the inside of said solvent bottle is pressurized internally. Said sleeve is provided with two restricting slots arranged at the two sides of the sleeve and symmetrical to the axis of the sleeve. The restricting slots comprise a first restricting slot and a second restricting slot, which are upside down "L"-shaped. Two buckles symmetrical to the axis of the plunger sleeve and vertical to the end face of the plunger sleeve are arranged on the plunger sleeve integrated with the plunger and are inserted into the first restricting slot or the second restricting slot respectively.

Said syringe for powder medicament premixing according to the present invention, in which the inside of said solvent bottle is under normal pressure. Said sleeve is provided with restricting slots, which comprise two "L"-shaped sections communicating with each other. The plunger sleeve integrated with the plunger is provided with buckles, which are inserted into the shorter portion on the upper end of the restricting slots. A viewing port is longitudinally arranged on the sleeve. The cross-section of the sleeve is of round shape, square shape, rectangular shape, ellipse shape, triangle shape, pentagon shape, or hexagon shape but with inner round shape, etc.

Said syringe for powder medicament premixing according to the present invention, in which the inside of said solvent bottle is under normal pressure. Said restricting slots are embedded in the inner wall of the sleeve. The restricting slots comprise two "L"-shaped sections communicating with each other. The cross-section of the sleeve is of round shape, square shape, rectangular shape, ellipse shape, triangle shape, pentagon shape, or hexagon shape, but with inner round shape, etc.

Said syringe for powder medicament premixing according to the present invention, in which the inside of said solvent bottle is under normal pressure. Said sleeve is provided with two restricting slots arranged at the two sides of the sleeve and symmetrical to the axis of the sleeve. The restricting slots comprise two "L"-shaped sections communicating with each other. Two buckles are symmetrically arranged on the plunger sleeve that is integrated with the plunger. Said two buckles are inserted into the shorter portion of the upper end of the two restricting slots respectively. The sleeve is provided with two viewing ports arranged symmetrically to the axis of the sleeve in the longitudinal direction.

Said syringe for powder medicament premixing according to the present invention, in which the inside of said solvent bottle is under normal pressure. Said sleeve is provided with two restricting slots embedded in the two inner sides of the sleeve and symmetrical to the axis of the sleeve. The restricting slots comprise two "L"-shaped sections communicating with each other. Two buckles symmetrically arranged on the plunger sleeve that is integrated with the plunger. Said two buckles are inserted into the shorter portion of the upper end of the two restricting slots respectively. The sleeve is provided with two viewing ports arranged symmetrically to the axis of the sleeve in the longitudinal direction.

DETAILED DESCRIPTION OF THE PREFERRED EMBODIMENTS

Advantages and features of the present invention will become apparent from the following detailed descriptions of the invention in conjunction with the accompanying drawings.

Embodiment 1

Figure 10:
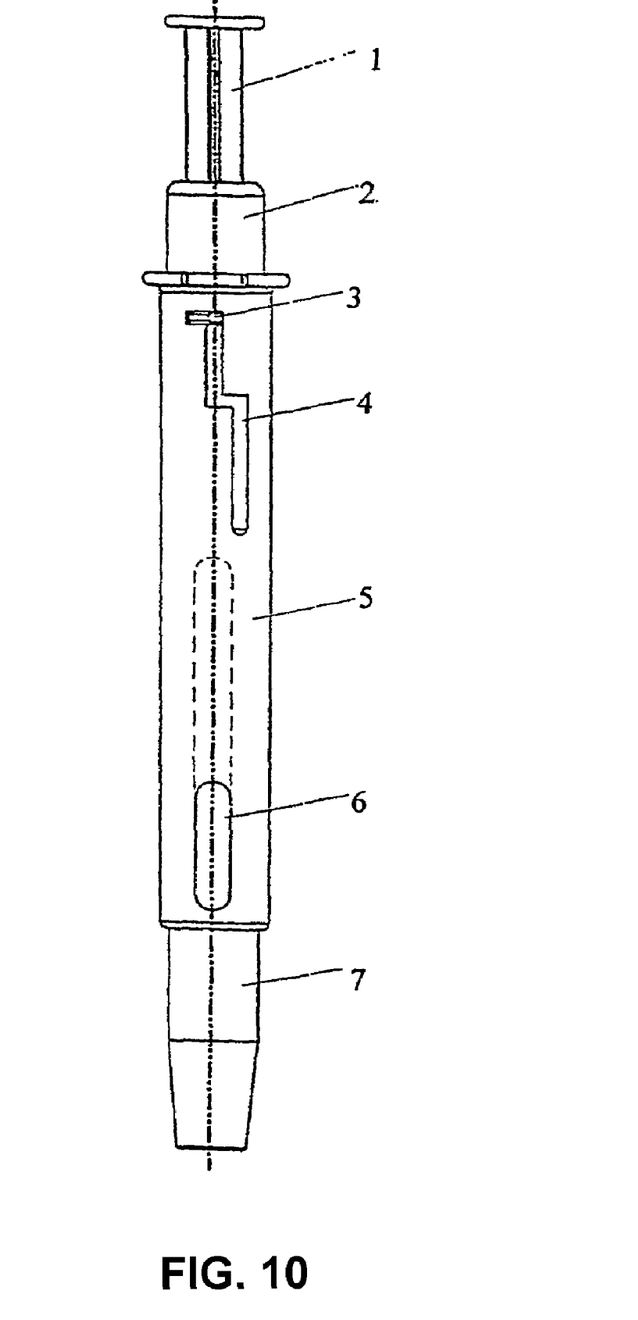
FIG. 10 is a schematic view of the external structure of the solvent bottle with normal pressure according to the present invention.
Figure 11:
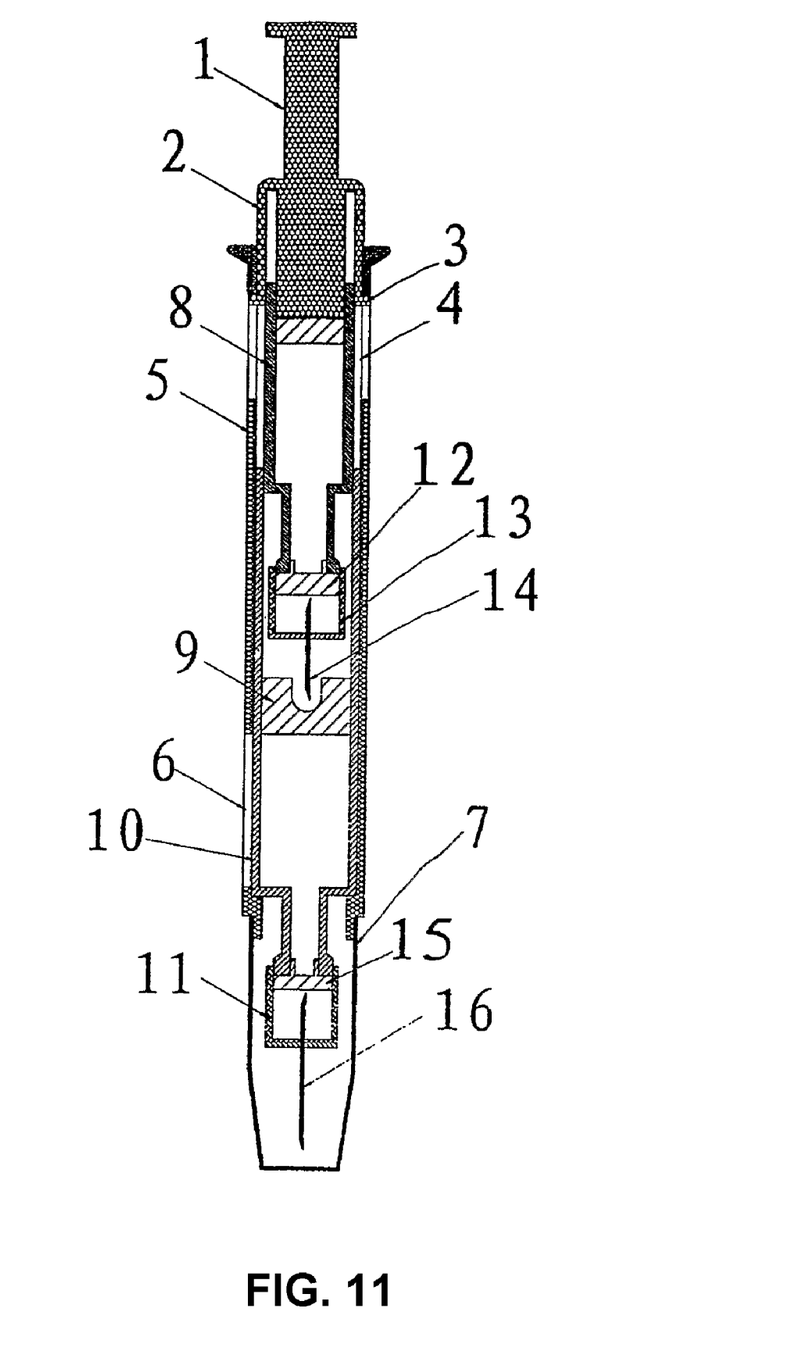
FIG. 11 is a schematic view of the internal structure of the solvent bottle with normal pressure according to the present invention.

FIGS. 10 and 11 show a syringe for premixing and administering powder medicament according to the present invention. The syringe basically comprises a plunger 1, a cylindrical sleeve 5, a solvent bottle 8, a connecting tube 14, a solute bottle 10 and a syringe needle 16 having two piercing ends. The solvent bottle 8 containing a diluent 18 is not pressurized and is under normal pressure. The plunger 1 is provided above the sleeve 5 and the solvent bottle 8. Both the solvent bottle 8 and the solute bottle 10 are packaged inside the sleeve 5. The solvent bottle 8 is positioned on the solute bottle 10 and is partially inserted and slidably fitted into the solute bottle 10. The lower end of the solute bottle is connected with the syringe needle 16.

Two restricting slots 4 are formed on the sleeve 5 symmetrical to the central axis of the sleeve 5. The restricting slots 4 comprise two "L"-shaped right angle portions communicating with each other. The longer section of a first "L"-shaped portion of the restricting slots is long enough to allow the needle-like connecting tube 14 to pierce through a sealing plug 12 and a piston 9. The longer section of the second "L"-shaped portion of the restricting slots facilitates a nurse to control the piercing depth of the needle. The shorter sections of the first and the second "L"-shaped portions of the restricting slots are designed for self-locking, that is, a plunger sleeve 2 integrated with the plunger 1 is provided with two symmetrically arranged buckles 3, which are inserted into the shorter sections of the "L"-shaped portions of the restricting slots 4 and are fitted with the restricting slots 4 in a slidable fashion to achieve self-locking. The buckles 3 are located inside the shorter section of the upper end of the restricting slot 4 to keep it in a self-locking status before use. A viewing port 6 is longitudinally provided on the sleeve 5 to observe the mixing of the powder with the diluent. The viewing port 6 can be configured longer as shown by the dashed lines in FIG. 10 to observe the connecting tube 14 piercing through the sealing plug 12 and the piston 9.

A piston 17 is provided inside the solvent bottle 8 at the upper end and is located under the plunger 1. The hollow connecting tube 14 with two piercing ends is provided between the solvent bottle 8 and the solute bottle 10. One end of the connection tube 14 is fixed on a bracket 13 located on the lower end of the solvent bottle 8. Two protrusions 25 are formed on two inner sides of the bracket 13. Protrusions 25 are in contact with the bottom opening of the solvent bottle 8. The bottom opening of the solvent bottle 8 and the solute bottle 10 are provided respectively with sealing plugs 12 and 15 made of surgical rubber or innoxious rubber. Guiding recesses 26 and 29 are formed on the central portions of the sealing plugs 12 and 15 respectively. The piston 9 is provided inside the solute bottle 10 and is located under the solvent bottle 8. One end of the syringe needle 16 is fixed to the bracket 11 plugged into the lower end of the solute bottle 10. Two protrusions 28 are formed on the two inner sides of the bracket 11. The protrusions 28 are in contact with the bottom opening of the solute bottle 10. The protrusions 25 and 28 are in the form of protruding nipples. The protecting jacket 7 covers the sealing plug 15, the bracket 11 and the syringe needle 16.

When in use, the plunger 1 is rotated to make the buckle 3 locate on the upper end of the restricting slot 4, then the plunger 1 is pressed by hand until the buckle 3 moves along the restricting slot 4 to the lower end of the first portion, then the solvent bottle 8 is applied with pressure through the plunger sleeve 2, so that the needle-like connecting tube 14 fixed on the bracket 13 will pierce through the sealing plug 12 and the piston 9 when the connecting tube 14 is moving with the bracket 13. Now the solvent bottle 8 and the solute bottle 10 are communicated with each other via the connecting tube 14. The diluent will enter the solute bottle to dissolve and mix the powder medicament uniformly under the pressure inside the solvent bottle 8 generated by pressing the plunger 1. The protecting jacket 7 is then removed and the syringe needle 16 is injected into the patient, or a transfusion bottle or a transfusion tube. The plunger 1 is rotated again so that the buckles 3 enter the second portion of the restricting slot 4. Then the plunger 1 is pushed again to make the piston 9 move downwardly so that the mixed medicament is forced into the muscle of a patient or a transfusion bottle or a transfusion tube through the syringe needle 16 to finish a complete operation. Because the syringe needle 16 is fixed to the bracket 11, the bracket 11 will move upwardly to make the syringe needle 16 pierce through the sealing plug 15 of the solute bottle 10 when the syringe needle 16 is injected into the patient or the transfusion bottle. Thus the mixed medicament may enter a human body or a transfusion bottle or tube.

The solvent bottle 8 and the solute bottle 10 are integrated inside the sleeve 5 to form an assembly. The assembly can be used only once and should be discarded after use. In fact it is a self-destructive syringe. It is very safe and the problem of cross-contamination can be avoided.

Embodiment 2

The inside of the solute bottle 10 is under normal pressure. The restricting slot 4 is fitted into the inner wall of the sleeve 5. The shape of the cross section of the sleeve 5 is of round shape, rectangle shape, square shape, ellipse shape, triangle shape, pentagon shape, or hexagon shape but with inner round shape. Said protrusions 25 and protrusions 28 are three protruding fins or hooks. Other configurations are similar to that of embodiment 1.

Embodiment 3

Figure 12:
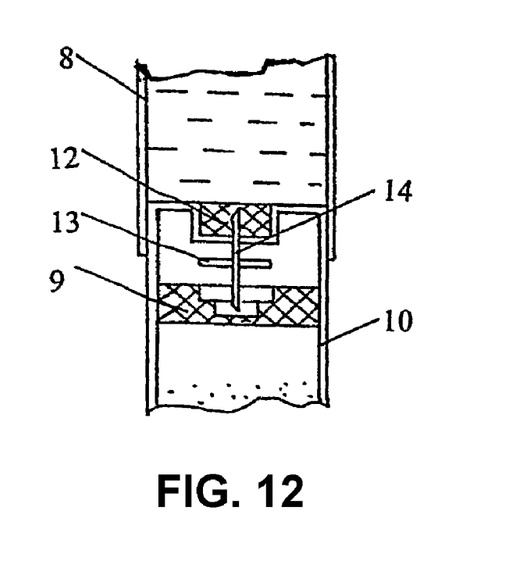
FIG. 12 is a schematic view of the solute bottle inserted into the solvent bottle with normal pressure according to the present invention.

As shown in FIGS. 10 and 12, the inside of the solvent bottle 8 is under normal pressure, in which the solute bottle 10 is inserted into the solvent bottle 8. Said protrusions 25 and protrusions 28 are each of five numbers. Other configurations are similar to those of embodiment 1.

Embodiment 4

Figure 13:
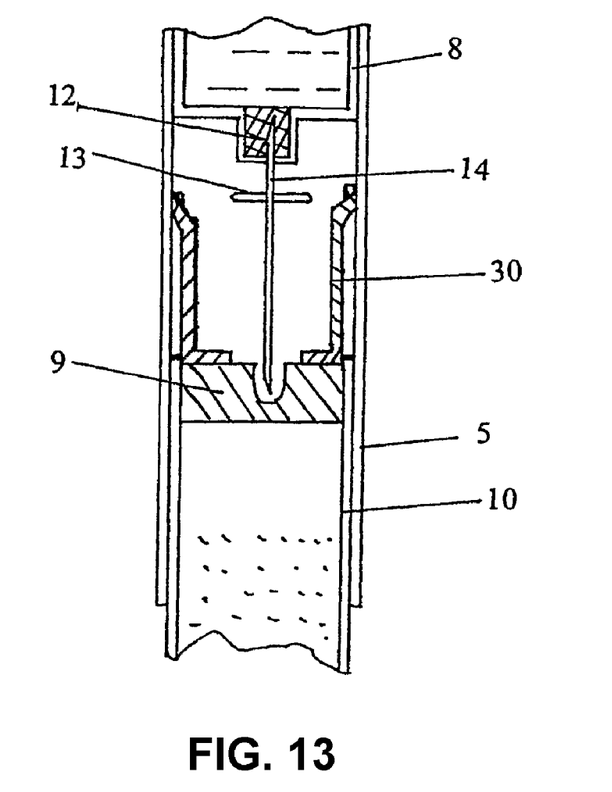
FIG. 13 is a schematic view of the solute bottle having same diameter as the solvent bottle with normal pressure according to the present invention.

As shown in FIGS. 10 and 13, the inside of the solute bottle 10 is under normal pressure, in which the solvent bottle 8 and the solute bottle 10 have the same outer diameter. A pushing sleeve 30 is provided on the upper edge of the piston 9 of the solute bottle 10. Said protrusions 28 and protrusions 25 are each of three numbers and are in a shape of protruding rings. Other configurations are similar to those of embodiment 1.

Embodiment 5

Figure 1:
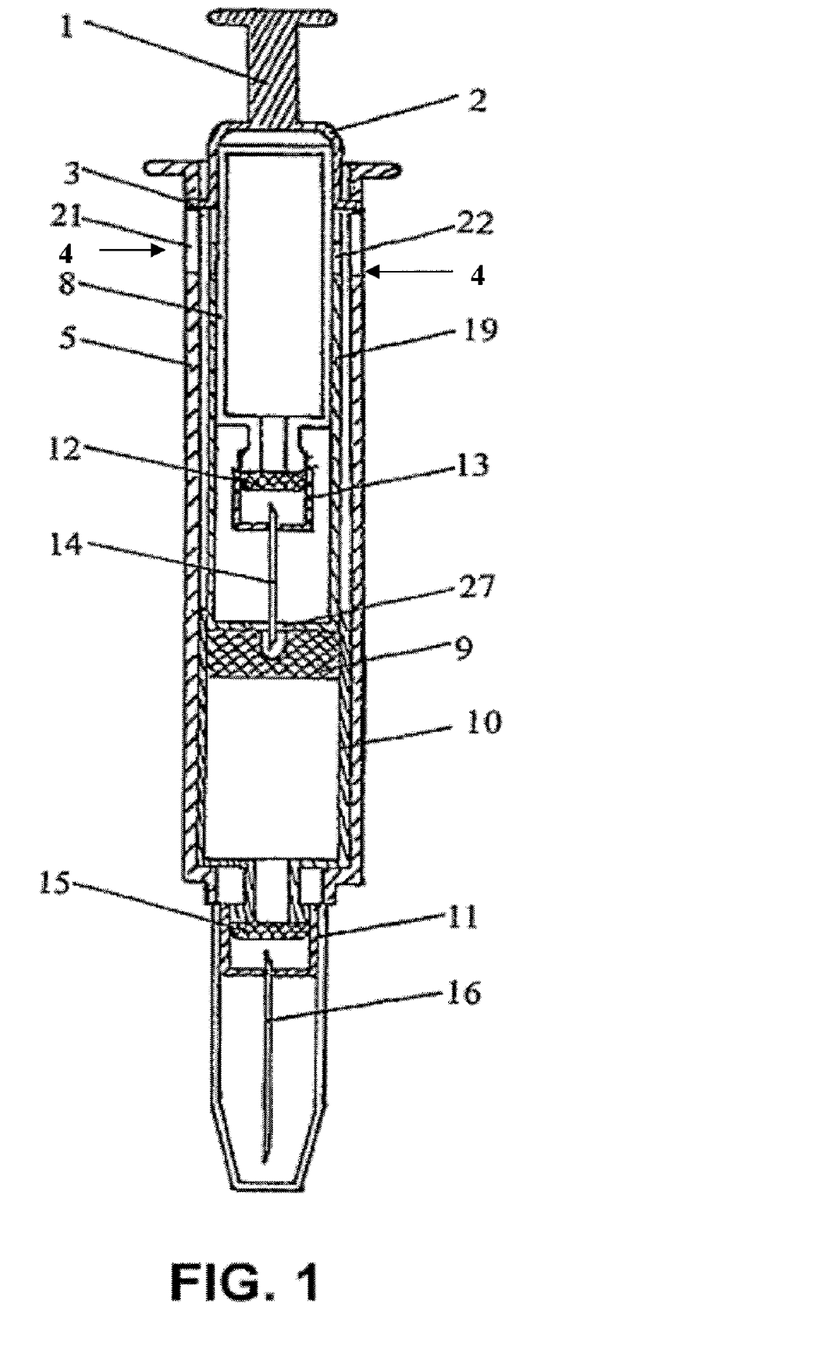
FIG. 1 is a schematic view of the solvent bottle with internal pressure according to the present invention.

As shown in FIG. 1, this embodiment is characterized in that the inside of the solvent bottle 8 is applied with pressure.

Figure 6:
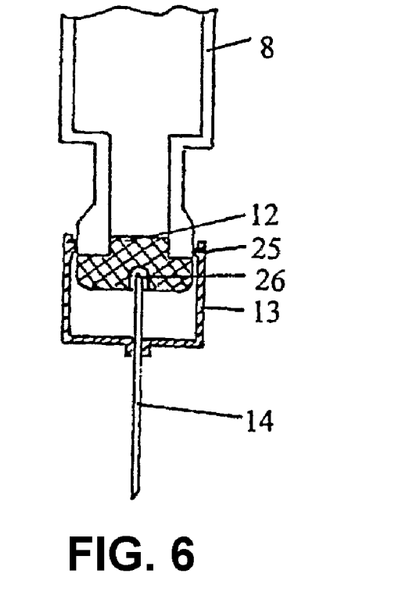
FIG. 6 is a schematic view of the solvent bottle with internal pressure with the bracket fixing the connecting tube in the initial position according to the present invention.
Figure 7:
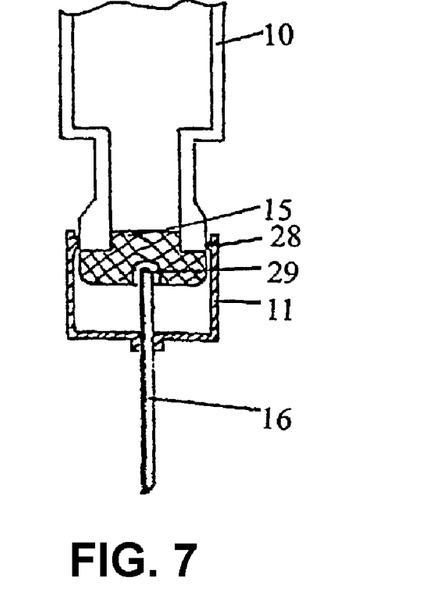
FIG. 7 is a schematic view of the solvent bottle with internal pressure with the bracket fixing the two-ended syringe needle in the initial position according to the present invention.
Figure 8:
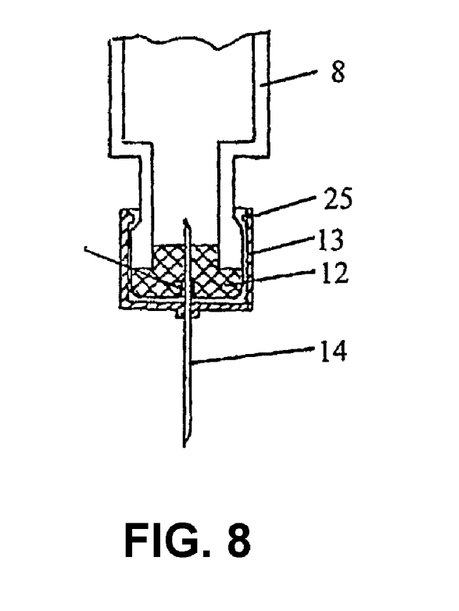
FIG. 8 is a schematic view of the solvent bottle with internal pressure with the bracket fixing the connecting tube in buckle position B according to the present invention.
Figure 9:
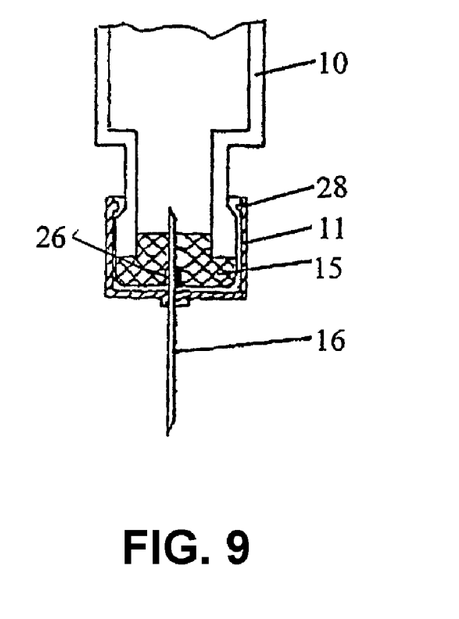
FIG. 9 is a schematic view of the solvent bottle with internal pressure with the bracket fixing the two-ended syringe needle in buckle position D according to the present invention.

The solvent bottle 8 is inserted into an inner sleeve 19 and is able to move along the inner sleeve 19. Both the solute bottle 10 and the inner sleeve 19 are provided inside the sleeve 5. The lower end face of the inner sleeve 19 is provided with a hole 27 and is in contact with the piston 9. The syringe comprises a plunger, a sleeve, a solvent bottle 8, a connecting tube 14, a solute bottle 10 and a syringe needle 16 with two piercing ends, in which the plunger 1 is provided on the upper portion of the sleeve 5 and the solvent bottle 8. Both the solvent bottle 8, which is provided above the solute bottle 10, and the solute bottle 10 are packaged in the sleeve 5. The syringe needle 16 having two piercing ends is connected to the bottom portion of the solute bottle 10. The connecting tube 14 with two piercing ends is provided between the solvent bottle 8 and the solute bottle 10. One piercing end of the connecting tube 14 is fixed to a bracket 13 plugged into a bottom opening of the solvent bottle 8. As shown in FIG. 6, three protrusions 25 are formed on the inner side of the bracket 13. The protrusions 25 are in contact with the bottom opening of the solvent bottle 8. As shown in FIGS. 1, 6 and 8, the bottom opening of the solvent bottle 8 is provided with a sealing plug 12 made of surgical rubber or innoxious rubber. The central portion of the sealing plug 12 is provided with a guiding recess 26. As shown in FIGS. 1, 7 and 9, the bottom opening of the solute bottle 10 is provided with a sealing plug 15 made of surgical rubber or innoxious rubber. The central portion of the sealing plug 15 is provided with a guiding recess 29. A piston 9 is contained inside the solute bottle 10. As shown in FIG. 1, one piercing end of the syringe needle 16 is fixed to a bracket 11 plugged into the bottom opening of the solute bottle 10. As shown in FIGS. 7 and 9, the inner side of the bracket 11 is provided with three protrusions 28, which are in contact with the bottom opening of the solute bottle 10. The sealing plug 15, the bracket 11 and the syringe needle 16 with two piercing ends are covered with a protecting jacket 7. The protrusions 25 and 28 can be protruding rings. Any configuration that allows for moving along the bottle opening and being locked with the step formed outside the bottle opening are acceptable.

Figure 2:
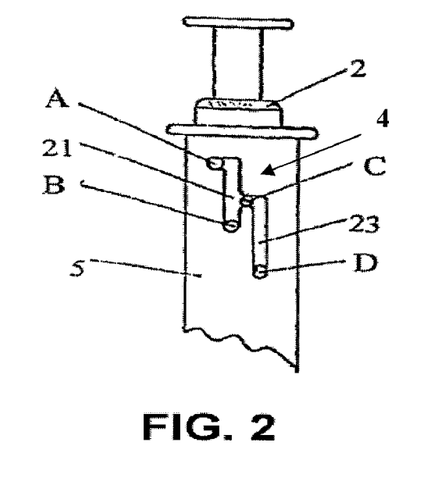
FIG. 2 is a schematic view of the restricting slot and the buckle of the solvent bottle with internal pressure according to the present invention.

As shown in FIGS. 1 and 2, two restricting slots 4 are symmetrically arranged at the two sides of sleeve 5 symmetrical to the central axis of the sleeve 5. The restricting slots 4 comprise a first restricting slot 21 and a second restricting slot 23 which are an upside down "L"-shape and communicate with each other. The plunger sleeve 2 integrated with the plunger 1 is provided with two buckles 3 fitted into and moving along the first restricting slot 21 and the second restricting slot 23 respectively. The buckles 3 are arranged vertical to the circumferential end face of the plunger sleeve and symmetrical to the axis of the plunger sleeve 2.

Figure 3:
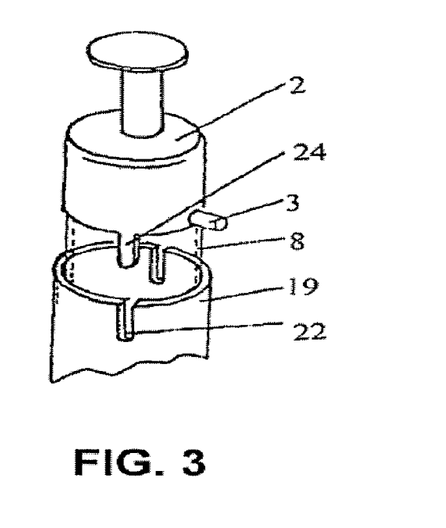
FIG. 3 is a schematic view of the solvent bottle with internal pressure with the buckle at position A according to the present invention.
Figure 4:
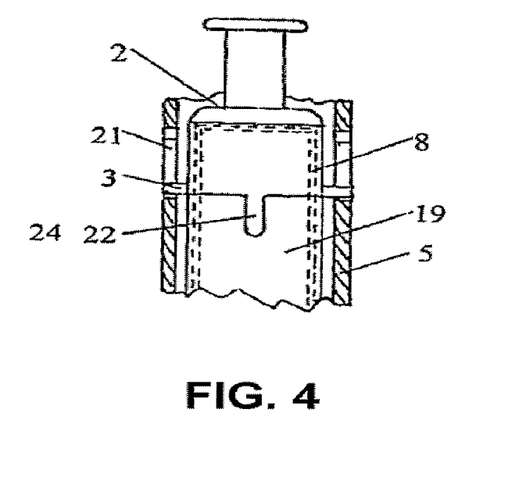
FIG. 4 is a schematic view of the solvent bottle with internal pressure with the buckle at position B according to the present invention.
Figure 5:
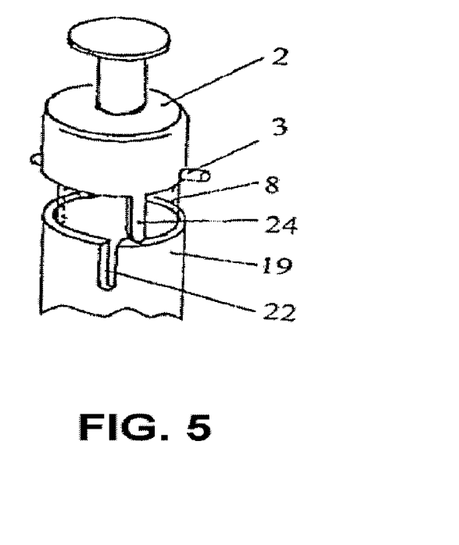
FIG. 5 is a schematic view of the solvent bottle with internal pressure with the buckle at position C according to the present invention.

As shown in FIGS. 3, 4 and 5, two tongues 24 are arranged on the two sides of the lower edge of the plunger sleeve 2 and symmetrical to the axis thereof. Two slots corresponding to the positions of the tongues 24 are arranged on the two sides of the upper edge of the plunger sleeve 2 and symmetrical to the axis thereof. The tongues 24 are inserted into the slots 22 respectively. The cross-section of the sleeve is of round shape.

During the preparation of the present embodiment, the solute bottle 10 contained with powder medicament 20 and the solvent bottle 8 contained with diluent 18 are packaged into the sleeve 5 in advance. In the initial state, the buckle 3 is located on the upper end of the first restricting slot 21, i.e. position A, as shown in FIG. 2 and FIG. 3.

When performing an injection, push the plunger 1 slightly to make the buckle 3 rotate into the first restricting slot 21. Then push the plunger 1 to make the solvent bottle 8 move along the inner sleeve 19 by pushing the plunger sleeve 2 until the buckle 3 reaches the end of the first restricting slot, i.e. position B. At this time, the tongue 24 is inserted into the slot 22 of the inner sleeve 19, as shown in FIG. 4. During this process, due to the effect of pressure, the connecting tube 14 having two piercing ends will pierce through the piston 9 and the sealing plug 12 so that solvent bottle 8 is communicated with the solute bottle 10. The diluent 18 inside the solvent bottle 8 will be automatically injected into the solute bottle 10 through the connecting tube 14 by the effect of inner pressure to dissolve powder medicament 20. At the same time, the bracket 13 moves along the bottom opening of the solvent bottle 8 until its end face is in contact with the sealing plug 12, as shown in FIG. 8. During this process, the inner sleeve 19 and the piston 9 move relative to each other and the syringe needle 16 having two piercing ends does not pierce through the sealing plug 15 yet.

After the above process, the plunger 1 is pulled up and rotated to make the buckle 3 reach the upper end of the second restricting slot 23 through the connecting portion between the first and the second restricting slots 21 and 23, i.e. position C. During this operation, the tongue 24 is detached from the slot 22 and the tongue 24 is moved to the upper edge of the slot 22. At the same time, because the plunger 1 is pulled up and the solvent bottle 8 and the bracket 13 are moved upwardly, the lower end of the connecting tube 14 is drawn out from the piston 9 to disconnect the communication between the solvent bottle 8 and the solute bottle 10 to avoid backflow of liquid medicament due to overpressure inside the solute bottle 10.

The next step is to inject the solution into a human body, a transfusion bottle or a transfusion tube. When the syringe needle 16 is injected into a human body or a transfusion bottle or tube, the counterforce is strong enough to make the bracket 11 slip along the bottom opening of the solute bottle until the end face of the bracket 11 is in contact with the sealing plug 15, as shown in FIG. 9. At this time, the syringe needle 16 has pierced through the sealing plug 15 and the buckle 3 moves along the second restricting slot 23 and down to the bottom end thereof, i.e. position D. By the force applied on the upper edge of the inner sleeve 19 by the tongue 24 of the plunger sleeve 2, the end face of the inner sleeve 19 is pressed against the piston 9 to make the liquid medicament inject into the human body or the transfusion bottle or tube via the syringe needle 16, thus to complete the process of injection.

Because protrusions 25 and 28 are arranged inside the brackets 13 and 11, when the end faces of the brackets 13 and 11 are in contact with the sealing plugs 12 and 15 respectively, the protrusions 25 and 28 are positioned to the step at the bottom opening of the solvent bottle 8 and the solute bottle 10 and are locked thereto; therefore the brackets 13 and 11 will not move back to their original positions when the plunger 1 is pulled up or when the syringe needle is drawn out from the human body, ensuring the proper operation and self-destruction for one-time use of the syringe according to the present invention.

The present invention has apparent advantages and benefits. It can be known from the above description that the present invention does not have the defects of the existing syringe. The structure of the present invention is more robust and variable for use. The present invention has the following advantages:

1. The syringe for medicament powder premixing according to the present invention integrates the solute bottle contained with medicament powder to the syringe needle with two piercing ends. The structure is simple and allows for easy operation, time saving, improved work efficiency, reduced intensity of work, and significantly lowered cost. At the same time, a nurse operating the syringe according to the present invention can be released from stress because misoperation and mistakes can be avoided.

2. The syringe for medicament powder premixing according to the present invention has a relatively simple structure and low additional production cost because it can be achieved by slightly changing the structure of the existing syringe. It is worthwhile comparing the added production cost with its great benefit. Therefore it has great industrial applicability.

3. The syringe for medicament powder premixing according to the present invention is safer in design. By fitting the restricting slots provided on the sleeve with the buckles provided on the plunger sleeve, it is has both position-limiting and locking functions. Thus, it is easy to control the force applied to the plunger when the bottles are communicating and to manage the depth of injection. The solute bottle and the solvent bottle are fixed to avoid loosening by engaging the buckles on the sleeve with the restricting slots on the plunger sleeve. Therefore, misoperation or damage during transportation and handling can be avoided. The syringe according to the present invention is more practical and meets the requirements of the normal syringe products.

Both the solute bottle and the solvent bottle of the syringe for medicament powder premixing according to the present invention are packaged inside the sleeve with a sealing plug and protecting jacket. The medicament powder and the diluent of predetermined dosage are contained in advance during production of the syringe. Therefore contamination and cross-infection can be avoided. The whole syringe is in an aseptic package and will not be in contact with air during operation. The syringe according to the present invention is designed to be used only once and then discarded.

The syringe for medicament powder premixing according to the present invention is provided with slots on both the plunger sleeve and the inner sleeve, and with a sliding construction of the bracket along the opening of the bottle. When the connecting tube is pulled out after the solvent bottle and the solute bottle have been connected, such construction can ensure that the medicament inside the solute bottle will not flow back and the bracket will not return to the original position after moving, so that such construction has a self-destruction function and can be used only once.

Having thus described several embodiments of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A syringe for powder medicament premixing, comprising
    a sleeve;
    a plunger that is provided on an upper portion of the sleeve;
    a solvent bottle that is positioned within said sleeve, said solvent bottle having a bottom opening that is provided with a first sealing plug that is made of a material selected from the group consisting of surgical rubber and innoxious rubber, a guiding recess being provided at a central portion of the first sealing plug;
    a solute bottle that is positioned within said sleeve, said solvent bottle being positioned above said solute bottle, said solute bottle having a bottom opening that is provided with a second sealing plug made of a material selected from the group consisting of surgical rubber or innoxious rubber and a guiding recess is provided at a central portion of the second seal plug,
    a piston being provided inside the solute bottle;
    a connecting tube, said connecting tube having two piercing ends and being provided between the solvent bottle and the solute bottle, one piercing end of the connecting tube being fixed to a bracket that is positioned in a bottom opening of the solvent bottle, at least two protrusions being formed on an inner side of the bracket, said protrusions being in contact with the bottom opening of the solvent bottle;
    a syringe needle having two piercing ends, one of said piercing ends being in communication with a bottom portion of said solute bottle, said piercing end being fixed to a bracket that is positioned in said bottom opening of the solute bottle and wherein at least two protrusions are formed on an inner side of the bracket, the protrusions being in contact with the bottom opening of the solute bottle; and wherein the second sealing plug, bracket and the syringe needle with two piercing ends are covered with protecting jacket; and
    wherein the sleeve is provided with restricting slots, the restricting slots including a first restricting slot and a second restricting slot, —both of which are upside-down "L"-shaped and communicate with each other, and a plunger sleeve is integrated with the plunger, said plunger sleeve being provided with buckles that are vertical to the plunger sleeve, the buckles being fitted into one of the first restricting slot or the second restricting slot, wherein two tongues are arranged on two sides of a lower edge of the plunger sleeve so as to be symmetrical to the axis thereof, and two slots corresponding to the positions of the tongues are arranged on the two sides of the upper edge of an inner sleeve so as to be symmetrical to the axis thereof.

2. The syringe according to claim 1, wherein said solvent bottle is provided inside the inner sleeve that is plugged into the solute bottle and both the solute bottle and the inner sleeve are positioned within the sleeve, the lower end face of the inner sleeve being formed with a hole that is defined in a piston.

3. The syringe according to claim 1, wherein a piston is provided on an upper end of the solvent bottle and under the plunger, and wherein one of the solvent bottle and the solute bottle is inserted into the other.

4. The syringe according to claim 1, wherein a piston is provided on an upper end of the solvent bottle and under the plunger, and wherein the outer diameters of the solvent bottle and the solute bottle are identical and a pushing sleeve is provided on the upper edge of the piston inside the solute bottle.

5. The syringe according to claim 1, wherein said restricting slots are arranged at two sides of the sleeve and symmetrical to an axis of the sleeve.

6. The syringe according to claim 1, wherein said buckles are inserted into a shorter portion on the upper end of the restricting slots.

7. The syringe according to claim 6, wherein a viewing port is longitudinally arranged on the sleeve, the cross-section of the sleeve.

8. The syringe according to claim 1, wherein said restricting slots are defined in an inner wall of the sleeve.

9. The syringe according to claim 6, wherein said sleeve is provided with two restricting slots that are arranged on the two sides of the sleeve and symmetrical to the axis of the sleeve, the restricting slots comprising two "L"-shaped sections communicating with each other, and wherein two buckles are symmetrically arranged on a plunger sleeve which is integrated with the plunger, and wherein said two buckles are inserted into the shorter portion of the upper end of the two restricting slots respectively, and wherein the sleeve is provided with two viewing ports that are arranged symmetrically to the axis of the sleeve in a longitudinal direction.

10. The syringe according to claim 8, wherein said sleeve is provided with two restricting slots that are embedded in the two inner sides of the sleeve and are symmetrical to the axis of the sleeve, the restricting slots comprising two "L"-shaped sections communicating with each other, and wherein two buckles are symmetrically arranged on the plunger sleeve which is integrated with the plunger, said two buckles are inserted into the shorter portion of the upper end of the two restricting slots respectively, and wherein the sleeve is provided with two viewing ports arranged symmetrically to the axis of the sleeve in longitudinal direction.

* * * * *